US008747662B2

(12) United States Patent
Delmage et al.

(10) Patent No.: US 8,747,662 B2
(45) Date of Patent: Jun. 10, 2014

(54) MODULAR HEMOFILTRATION APPARATUS WITH REMOVABLE PANELS FOR MULTIPLE AND ALTERNATE BLOOD THERAPY

(75) Inventors: J. Michael Delmage, Napa, CA (US); Harold Peters, Martinez, CA (US); Tommy Cooper, Friendswood, TX (US)

(73) Assignee: B. Braun Avitum AG, Melsungen (DE)

( * ) Notice: Subject to any disclaimer, the term of this patent is extended or adjusted under 35 U.S.C. 154(b) by 1160 days.

(21) Appl. No.: 12/183,527

(22) Filed: Jul. 31, 2008

(65) Prior Publication Data

US 2009/0084717 A1 Apr. 2, 2009

Related U.S. Application Data

(60) Provisional application No. 60/953,577, filed on Aug. 2, 2007.

(51) Int. Cl.
*B01D 35/00* (2006.01)

(52) U.S. Cl.
USPC ............... 210/90; 210/91; 210/108; 210/143; 210/201; 210/206; 210/235

(58) Field of Classification Search
None
See application file for complete search history.

(56) References Cited

U.S. PATENT DOCUMENTS

| 5,200,090 | A | | 4/1993 | Ford et al. |
| 5,437,624 | A | * | 8/1995 | Langley ........................ 604/6.05 |
| 5,441,636 | A | * | 8/1995 | Chevallet et al. ............. 210/232 |
| 5,605,627 | A | | 2/1997 | Carlsen et al. |
| 5,679,245 | A | | 10/1997 | Manica |
| 5,910,252 | A | | 6/1999 | Truitt et al. |
| 6,200,485 | B1 | | 3/2001 | Kitaevich et al. |
| 6,659,973 | B2 | | 12/2003 | Gorsuch et al. |
| 6,849,183 | B2 | | 2/2005 | Gorsuch et al. |
| 7,223,338 | B2 | | 5/2007 | Duchamp et al. |
| 7,232,418 | B2 | | 6/2007 | Neri et al. |
| 7,247,146 | B2 | | 7/2007 | Tonelli et al. |
| 2004/0034317 | A1 | * | 2/2004 | Gorsuch et al. .............. 604/5.01 |
| 2004/0084358 | A1 | * | 5/2004 | O'Mahony et al. ............. 210/94 |
| 2004/0127840 | A1 | | 7/2004 | Gara et al. |
| 2006/0084906 | A1 | * | 4/2006 | Burbank et al. ............. 604/6.16 |
| 2007/0278155 | A1 | | 12/2007 | Lo et al. |
| 2010/0089806 | A1 | | 4/2010 | Peters et al. |
| 2010/0094192 | A1 | | 4/2010 | Peters et al. |
| 2010/0094194 | A1 | | 4/2010 | Peters et al. |

OTHER PUBLICATIONS

Seuoka, A., "Present Status of Apheresis Technologies: Part 2. Membrane Plasma Fractionator," *Therapeutic Apheresis*, vol. 1, No. 2, May 1997, pp. 135-146.
Notice of Allowance mailed Oct. 4, 2012, for U.S. Appl. No. 12/577,513.

* cited by examiner

*Primary Examiner* — Dirk Bass
(74) *Attorney, Agent, or Firm* — RatnerPrestia

(57) ABSTRACT

An apparatus for performing blood therapy having a plurality of pumps for engaging blood and fluid tubing is characterized by a plurality of manually mounted and disengagable panels installed on the sides of the apparatus housing, the panels having pump engaging tubing mounted on the inside of the respective panels.

49 Claims, 11 Drawing Sheets

MODULAR HEMOFILTRATION APPARATUS WITH REMOVABLE PANELS FOR MULTIPLE AND ALTERNATE BLOOD THERAPY

CROSS-REFERENCE TO RELATED APPLICATIONS

This application claims priority to U.S. Provisional Patent Application No. 60/953,577 filed Aug. 2, 2007 and incorporated herein by reference.

BACKGROUND OF THE INVENTION

Hemodialysis systems have been designed to carry out blood therapy procedures such as slow continuous ultrafiltration (SCUF), continuous veno-venous hemofiltration (CVVH), continuous veno-venous hemodialysis (CVVHD) or continuous veno-venous hemodiafiltration (CVVHDF). These therapies, referred to as CRRT, are designed for removal of metabolic waste and excess fluid from patients in fluid overload and who need renal support. Presently available extracorporeal blood treatment apparatus often requires inconvenient and time consuming setup procedures including cleaning and/or replacing the blood and/or fluid tubing for different patients and for different therapies. Such procedures may require the apparatus to be removed from a patient's bedside or room to another location, or replacing an apparatus with a system that is set up and configured for carrying out a specific therapy.

U.S. Pat. No. 5,910,252 describes an apparatus configured for performing the different blood therapies and provides means for selecting one of the therapies to be carried out. The described apparatus is an assembly of all pumps, tubing, multiple fluid supply reservoirs, waste fluid container and filter cartridge necessary for performing any one of the selected blood therapies.

U.S. Pat. No. 6,200,485 describes another multipurpose hemofiltration system comprising an assembly of a blood filter cartridge, pumps, fluid reservoir and waste fluid container, components for comparing the weights of the fluid reservoir and waste fluid container and means for controlling the pump operations and rate in response to the compared weights during the therapy.

A Prismaflex™ system marketed by Gambro of Lakewood, Colo. offers selection of different CRRT therapies. The system allows the user to select a prepackaged, preassembled assembly incorporating all of the components including specific column and type of filter membrane or membrane filter surface area and all preconnected tubing for carrying out the selected therapy.

SUMMARY OF THE INVENTION

The apparatus and system described herein provides a flexible treatment platform for performing several different therapies for separating and removing undesirable components from blood as well as plasma separation and plasma treatment including plasmapheresis and therapeutic apheresis. The basic apparatus is a lightweight, portable, modular assembly including a housing having a plurality of peristaltic pumps secured in the housing together with a computer/controller. Manually removable and replaceable panels are provided with tubing sets mounted on the panels and configured for easy installation and replacement on the modular housing. The tubing kits on each of the different panels are configured and formed to readily engage one or more of the peristaltic pumps and for being connected to or disconnected from a filter cartridge, fluid supply bags and waste bags. The system provides a method allowing the physician or therapist to select a therapy, manually install a selected fluid control panel and selected filter cartridge, and thereafter, if desired, quickly and efficiently change the therapy by manually exchanging a panel and/or filter, or replacing a clogged filter. Such features as well as others, methods, advantages and operations of the apparatus will be disclosed in the following Detailed Description.

DETAILED DESCRIPTION OF THE PREFERRED EMBODIMENTS

It is understood that different patients have different medical conditions that require a selected therapy, or multiple or alternating therapies. Such different therapies may also call for use of different filter cartridges or columns as well as different tubing routing and setups. Moreover, there may be a need to exchange filter cartridges or columns during a procedure if the cartridge has failed or has become clogged.

The apparatus described herein is designed for convenient setup to provide CRRT selection as well as plasma separation, plasma exchange (TPE) and plasma treatment, such as therapeutic apheresis (TA), and thereafter, if desired, efficiently and economically modify the apparatus configuration to carry out a different blood therapy or plasma treatment. A blood tubing panel and fluid tubing panels are provided with identification components which are sensed or read by the computer/controller capable of reading and identifying which tubing panel and filter column are installed and for displaying that information to inform a physician or therapist that the installed filter column and blood and fluid panels are capable of performing the desired therapy. When a different therapy is desired at any time, or if a filter column needs to be replaced for any reason, by simply disconnecting the tubing ends and/or the filter, and replacing the filter or a panel, the apparatus configuration change can be readily made without the necessity of removing the blood access and blood return devices from the patient and minimizing interruption of the therapy. For example, to treat acute congestive heart failure, the apparatus may be set up to initially remove only excess plasma water from the patient's blood by installing an ultrafilter cartridge and a fluid side panel configured to direct plasma water from the ultrafilter to a fluid waste bag. Following ultrafiltration, the apparatus may be modified to perform CVVH, CVVHD or CVVHDF on the same patient by switching filter cartridges, adding a saline supply reservoir and/or dialysate bag and, if desired, a plasma replacement fluid bag, and continuing the blood therapy with minimal interruption. Similarly, by simply replacing a hemofilter cartridge with a plasma separation cartridge and adding a plasma infusion bag, the apparatus is configured for plasma replacement therapy. Alternatively, the plasma may be treated by mounting therapeutic apheresis components.

Figure 1:
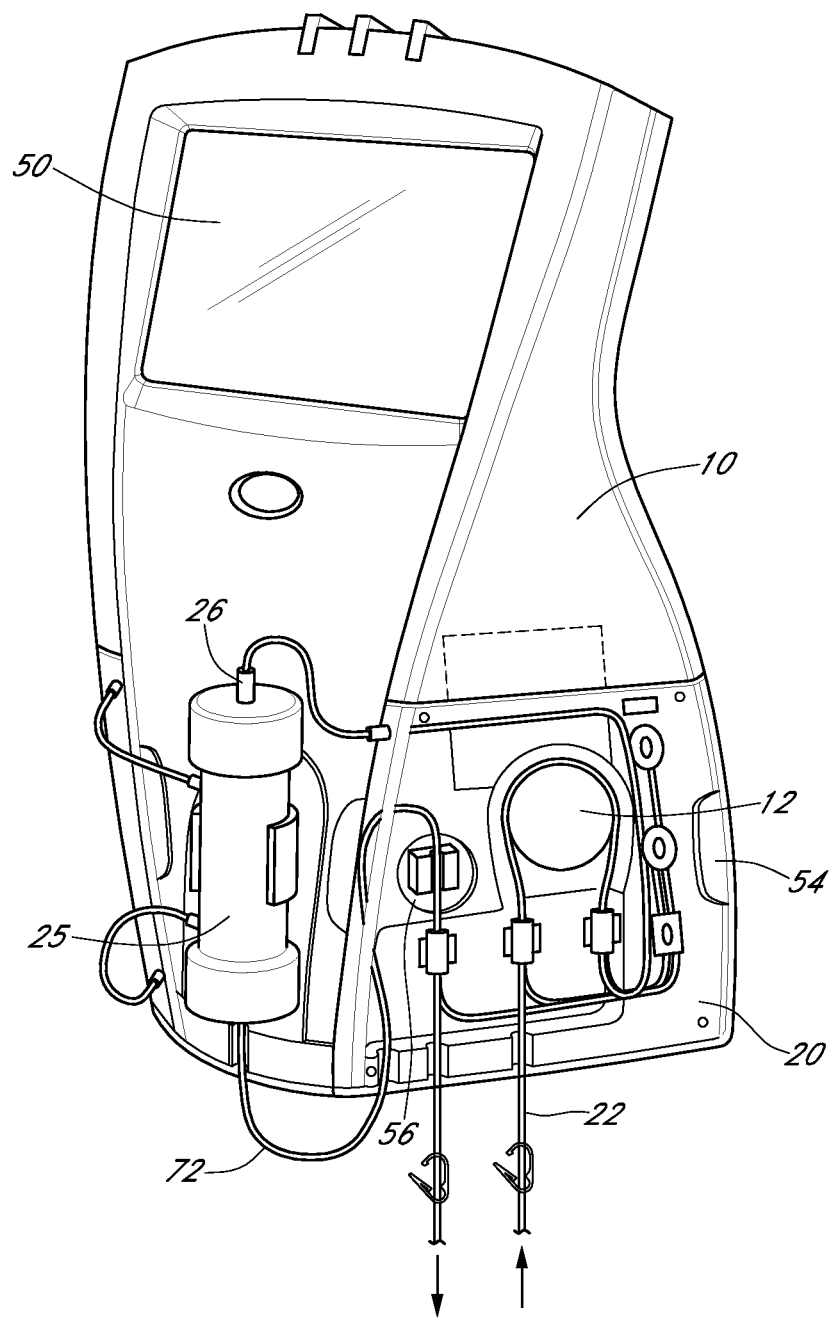
FIG. 1 illustrates one side and the front of the housing of the apparatus with a panel installed showing blood supply tubing engaging a blood pump.
Figure 2:
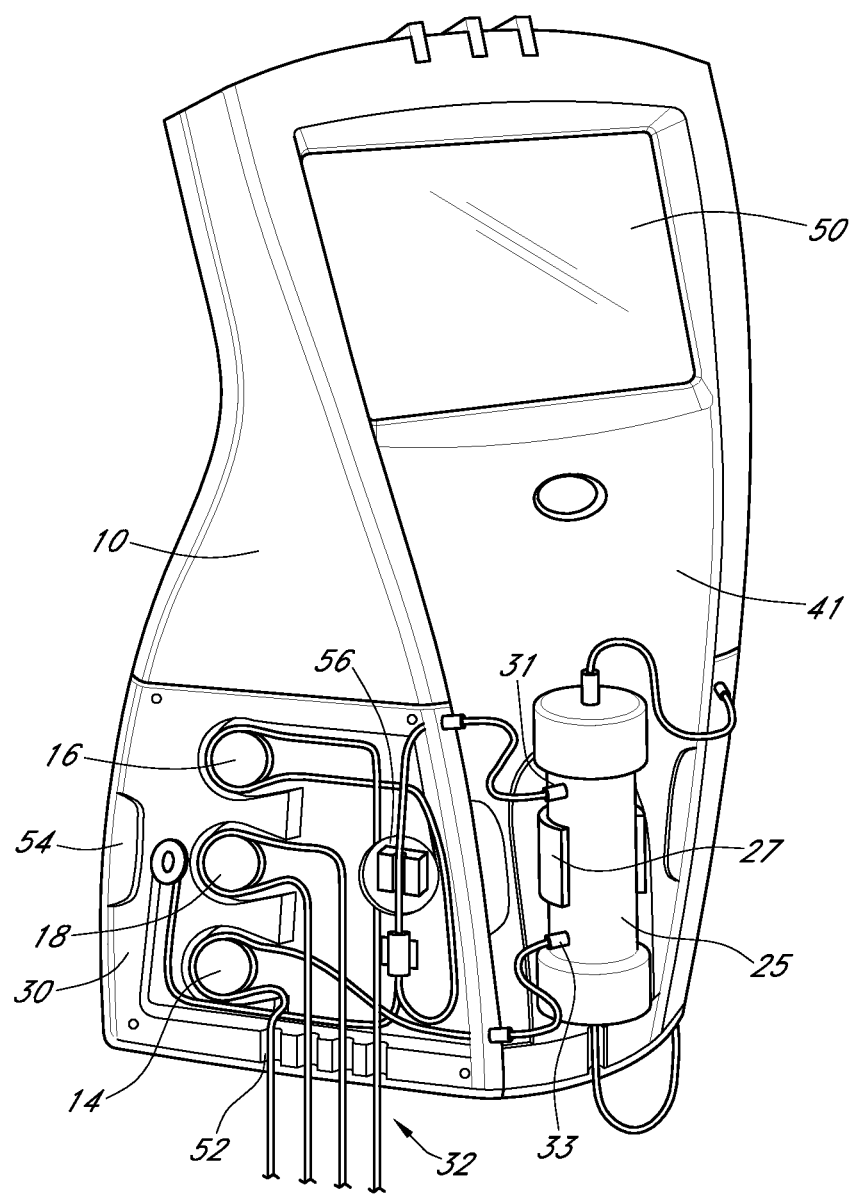
FIG. 2 illustrates another side of the housing assembly with a panel installed having fluid supply tubing engaging a plurality of peristaltic fluid pumps and connected to a filter cartridge.
Figure 3:
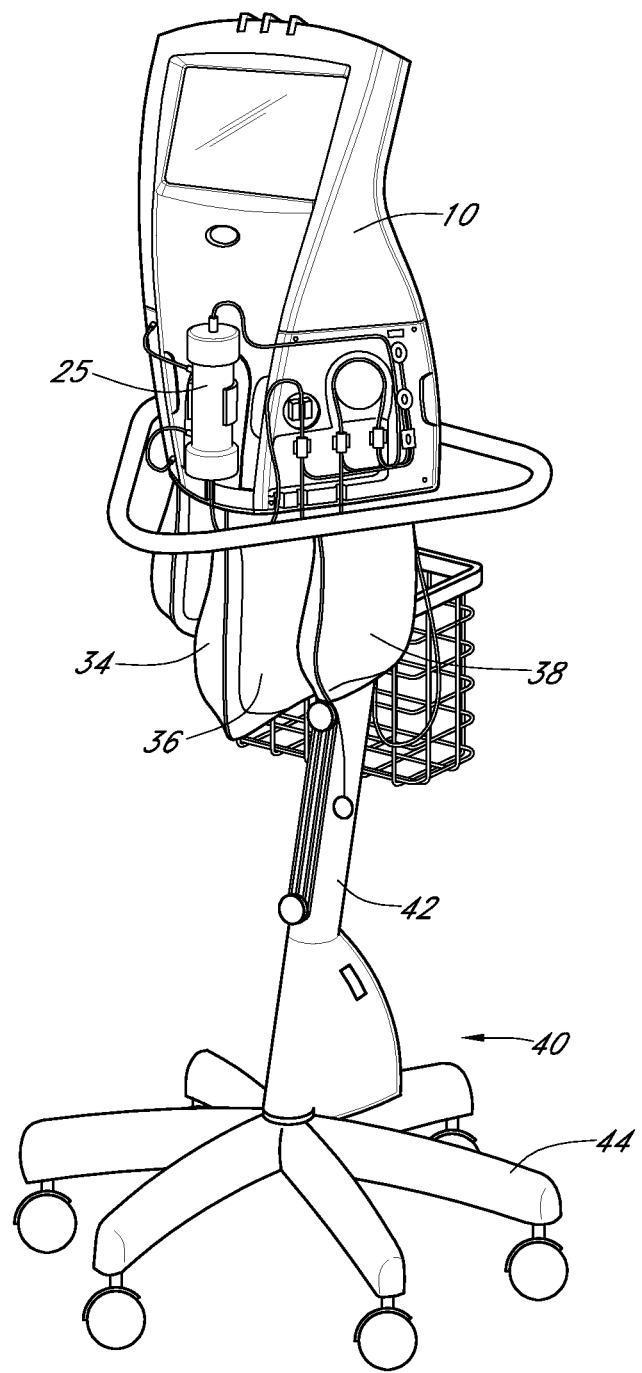
FIG. 3 illustrates the front and one side of the housing with a fluid supply bag and a collection bag mounted on a support pole and leg and caster assembly.

In FIGS. 1, 2 and 3 the housing assembly 10 is shown in which are secured the pumps, a computer/controller for operating the pumps and the system in carrying out the therapy, and to which housing the different removable and replaceable panels with mounted tubing are installed. In FIGS. 1 and 2, the front and sides of the housing assembly 10 are shown, the housing assembly including a screen 50 on which may be displayed information for guiding a user through operation of the system as well as notification of pump rates, alarms, and instructions on proceeding through operation of the blood therapy treatment. Preferably the screen is a touch screen provided with icons or other displays whereby the operation interacts with the computer by touching the screen to transmit the desired commands, instructions, or information. FIG. 1 shows the "blood side" of the housing assembly with manually mounted, removable and replaceable panel 20. Each panel is shaped to be easily manually installed and removed from an opening or cavity at the side of the housing. A panel preferably comprises a synthetic resin such as polycarbonate or other plastic and may be transparent or translucent to allow observation of the tubing on the inside of the installed panel. The blood side of the housing assembly includes a peristaltic blood pump 12 and blood tubing 22 mounted on the inside of the panel configured and shaped to engage a rotor of pump 12 when the panel is installed as shown.

FIG. 2 shows the "fluid side" of the housing assembly with panel 30 and fluid tubing 32. The fluid tubing is mounted on the inside of the panel and is configured and shaped to engage a plurality of different fluid pumps secured on the inside of the housing assembly. In the embodiment of FIG. 2, three peristaltic fluid pumps 14, 16 and 18 are shown with the fluid tubing 32 engaging the pumps with the panel 30 installed. Like panel 20 on the blood side of the housing assembly, panel 30 is similarly shaped for easy installation or removal from the housing assembly. As shown in FIGS. 1 and 2, the panels 20 and 30 include appropriate notches or recesses 52 to provide a pass-through for the tubing into and out of the housing. A handle recess 54 may be provided to allow an operator to grasp a panel during installation and removal. The various recesses and notches may be formed on the panels and/or the housing. Other openings such as holes or ports 56 are provided on the panel to allow observation and access to components positioned along the tubing such as air detectors and blood detectors. The tubing is conveniently secured on the interior or inside surface of each respective panel. For example, the tubing may be secured in slots, recesses or channels formed on the inside panel wall. Clips, brackets, hangers, etc. may also be used for securing the tubing. The tubing may also be secured by using any suitable adhesive, a UV curable adhesive or an ultrasonic weld between the panel wall and tubing that has been configured and shaped as desired.

Figure 7:
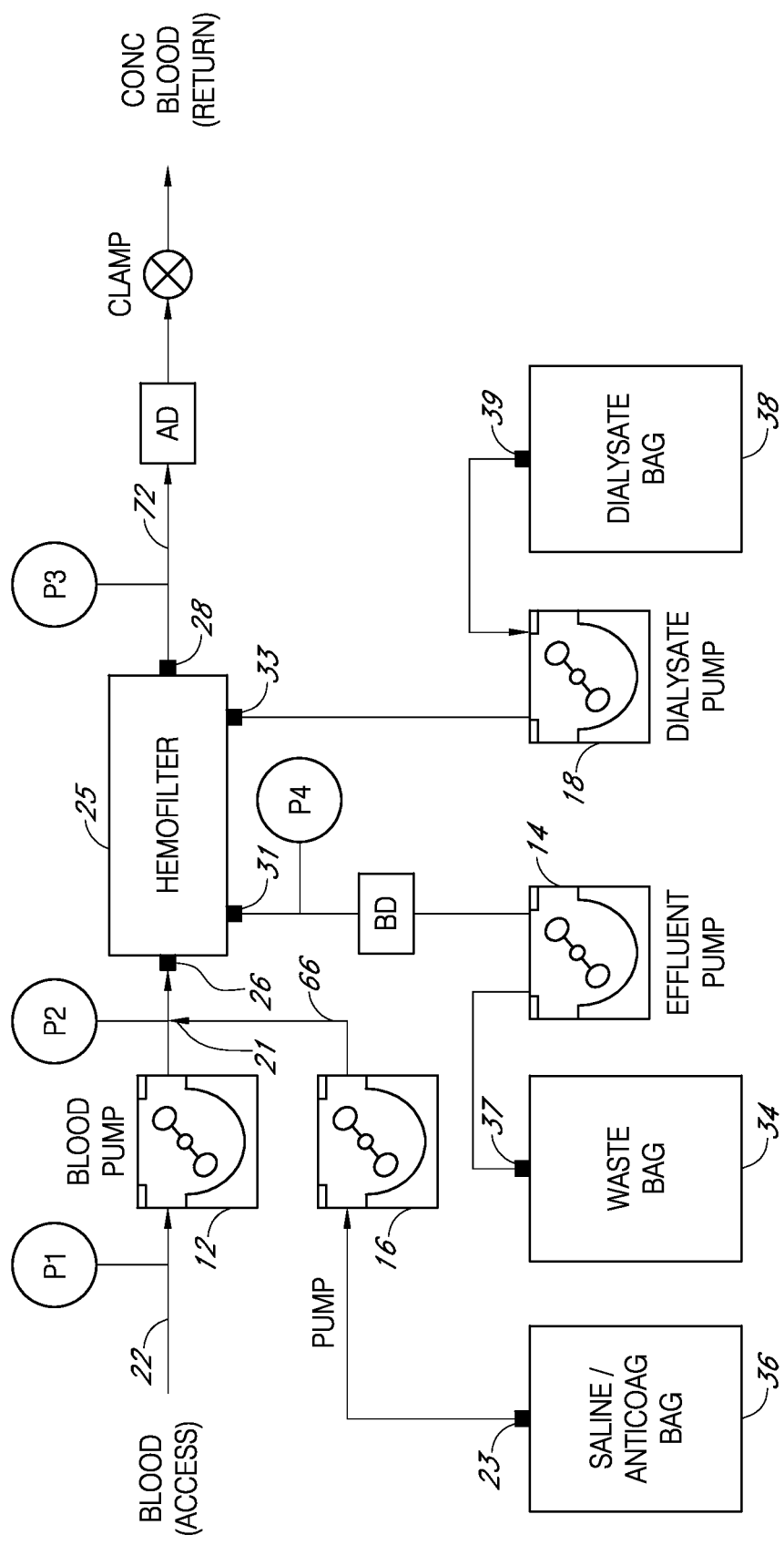
Figure 8:
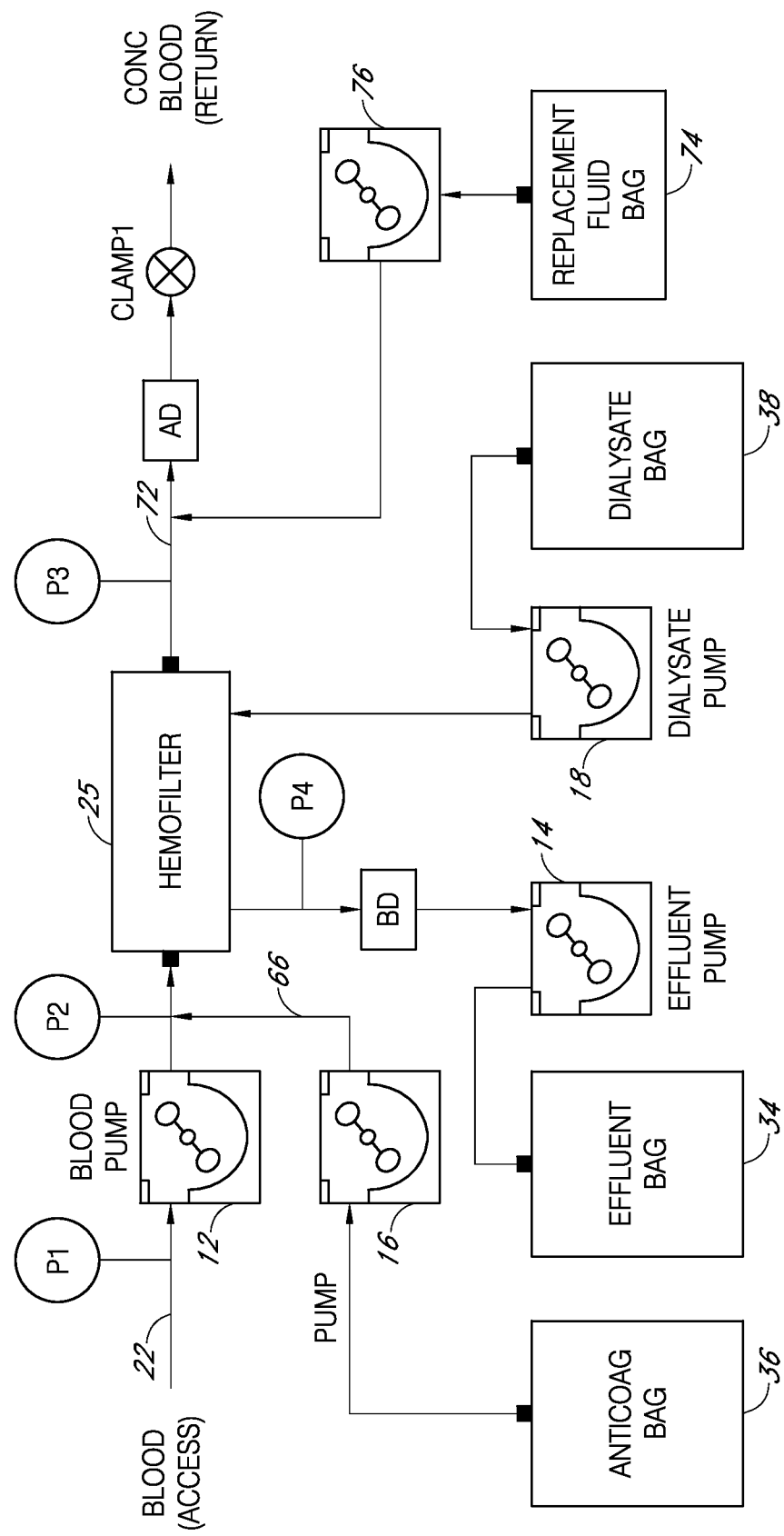
Figure 9:
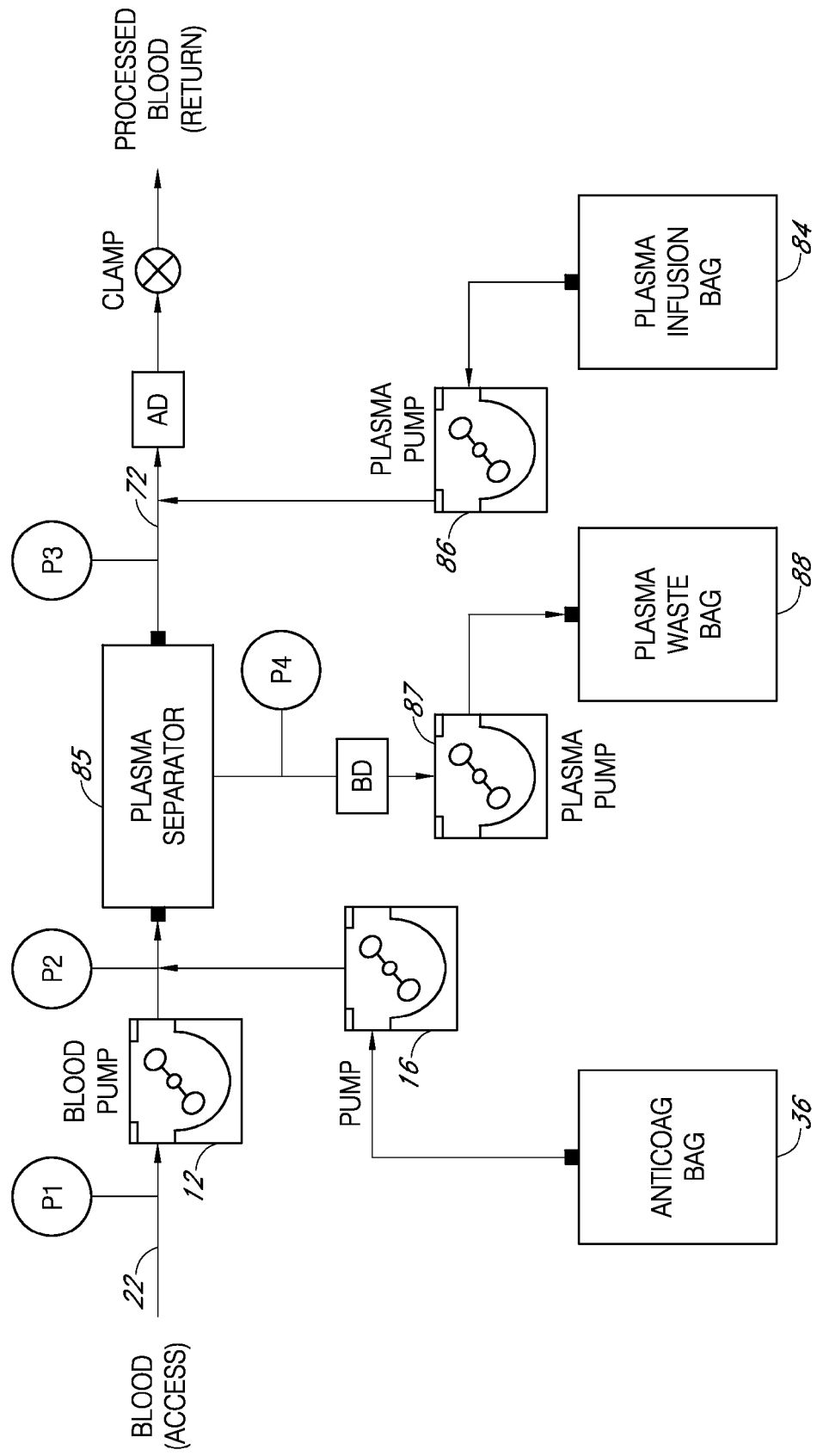
FIGS. 9 and 10 schematically illustrate plasma separation and plasma treatment apparatus embodiments.

FIG. 3 illustrates a preferred embodiment of the blood treatment apparatus which includes containers or bags 34, 36 and 38 for use in the treatment embodiments described and illustrated in FIGS. 7, 8 and 9. The apparatus includes a support column 42 as well as base 40 with legs 44 and casters.

Figure 4:
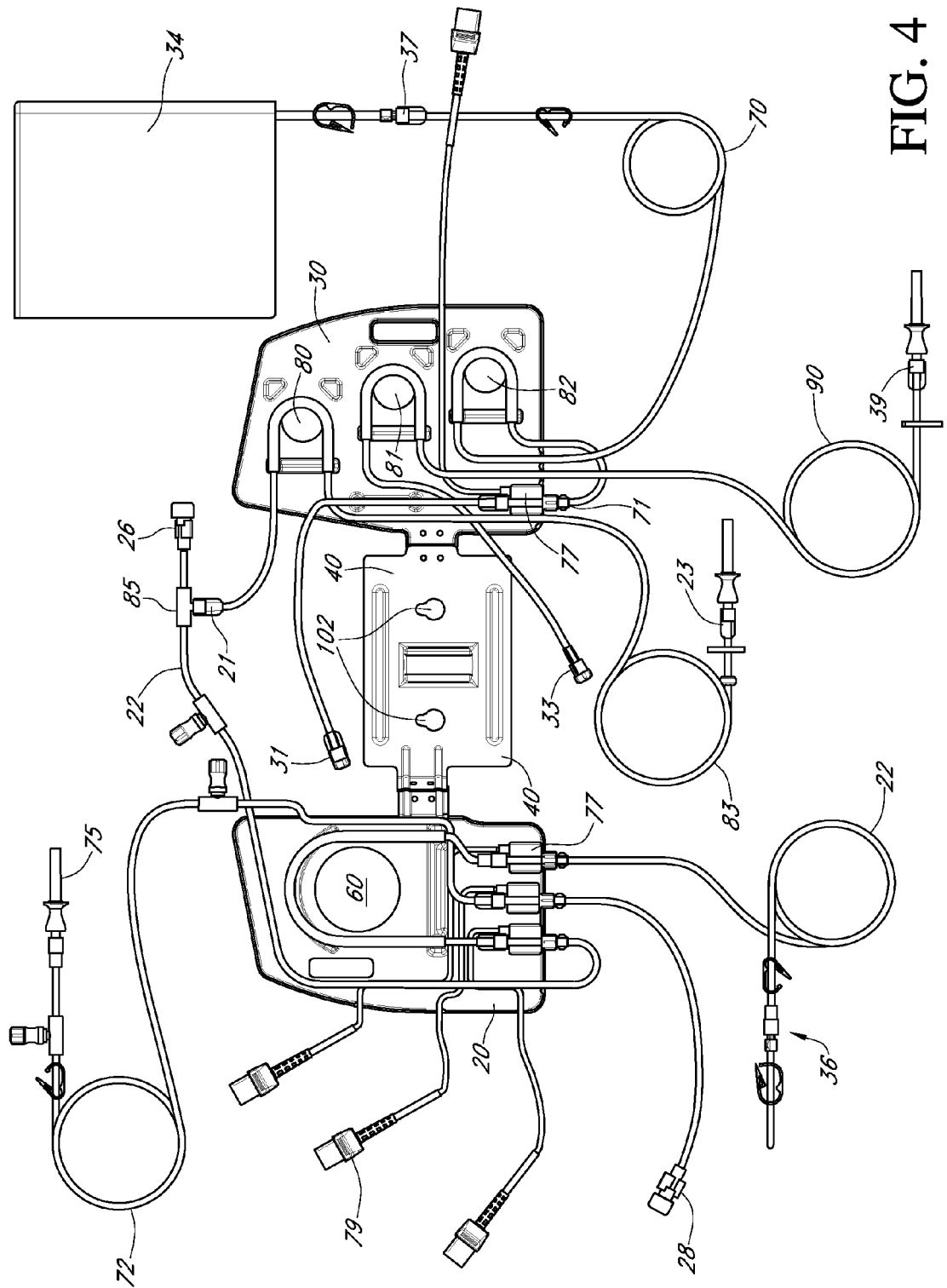
FIGS. 4 and 5 are drawings showing inside and outside views, respectively, of a panel assembly and component configurations.
Figure 5:
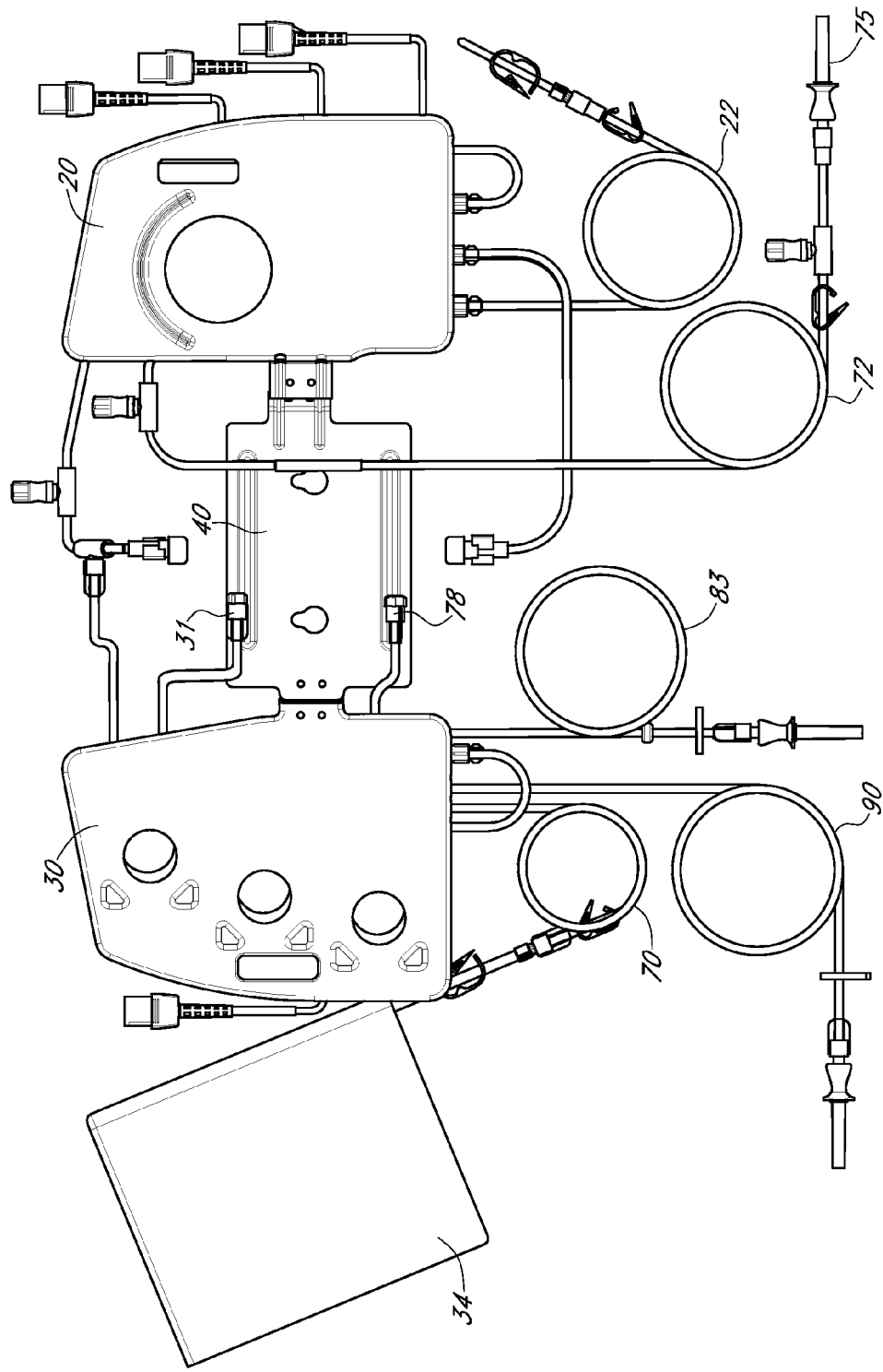

FIGS. 4 and 5 show inside and outside views, respectively, of preferred panel assembly embodiments. Panel 20 is the blood side panel having a large opening or port 60 for receiving a blood pump. Blood supply tubing 22 is looped around port 60 to cooperate with a rotor pump to pump blood from a patient to a filter column (not shown) to be connected to the tubing by connector 26. Blood return tubing 72 is provided with a connector 28 at one end for connecting to a filter column outlet port and a needle cannula assembly 75 at the opposite end for returning treated blood to a patient. Three pressure transducers 77 and transducer plugs 79 are also provided as are various tubing clamps. The apparatus will also include volume sensors, pressure sensors, blood leak detectors and air detectors connected along the tubing.

Fluid side panel 30 includes three fluid pump ports 80, 81 and 82 with tubing loops around each port for cooperating with the different fluid pumps. Effluent tubing 70 is provided with a connector 31 at one end for being connected to an effluent outlet on a filter column and a connector 37 at the opposite end for connection to a waste bag 34, which is an optional component of the panel assembly. A pressure transducer 71 is used along the effluent tubing. Tubing 83 will supply saline or replacement fluid from a bag or container. The saline may also contain an anticoagulant, and is pumped via a fluid supply pump at port 80 to a T connector 85 joining tubing 83 with blood supply tubing 22 downstream from a filter column (not shown). In the embodiment shown, a dialysate fluid supply tubing 90 is provided for supplying dialysate fluid to a hemofilter also configured for removing metabolic waste via diffusion as shown in FIG. 6 and as will be discussed hereinafter. Connector 33 at one end of the dialysate fluid tubing will be connected to a filter column. If only excess plasma water is to be removed from blood via simple ultrafiltration as described and shown in FIG. 5, the fluid panel may be configured without providing dialysate fluid tubing and even formed without a port for receiving a dialysate pump. However, in the process of molding a fluid panel, it is preferred to form a blank panel provided with three fluid pump ports and secure fluid tubing in the desired different configurations for different treatment options. A second optional bag is also shown which may be used as a priming waste bag. Bags for supplying replacement fluid such as saline, albumen or plasma, or for supplying dialysate fluid are normally supplied by the hospital, clinic, or treatment center. The bags are optional and may not be part of the panel assembly.

A third blank panel 40 is also shown on which a filter cartridge or column will be secured. A specific cartridge capable of carrying out a specific set of blood therapies may be mounted on the panel which is provided with a recess for receiving the cartridge and may also include clips, clamps, brackets or other components such as tape or a Velcro strap for securing a selected filter cartridge. Identification, e.g., bar code, may be on the filter cartridge, to be read by the computer to identify the type of cartridge and/or the procedures for which the cartridge is capable. The panels may be connected, for example, using hinges or flexible connectors or brackets as shown, or may be separated. A connected panel set allows the operator to mount the panel assembly components in a single operation, and also install and exchange selected filter cartridges on the blank center panel, as desired. The side panels may be provided with slots for receiving hangers, posts, brackets, clamps or other panel support members extending from the housing for mounting and supporting the panels. Front panel is provided with slots 102 for receiving mounting posts.

An alternative to the use of a third removable panel as described above on which a filter cartridge may be permanently or removably secured, the housing may be designed as illustrated in FIG. 2 whereby the front cover 41 of the housing is formed to provide a slot, recess or bracket 27 into which a filter cartridge 25 may be removably installed. The front cover of the housing may be also provided with clips, clamps or brackets for holding the removable cartridge in place in the recess, or an interchangeable bracket or tape or Velcro strap may be supplied for such a purpose. In such an embodiment, the front cover of the housing is also preferably provided with an opening or port through which computer sensible filter cartridge identification can be scanned or otherwise read or identified from within the housing. Alternatively, a filter cartridge identification scanning component may be installed on the front cover of the housing.

The tubing mounted in each of the respective blood and fluid panels are also provided with components for easily, quickly and efficiently connecting and disconnecting the tubing to other components of the apparatus. The ends of the different tubing sets are provided with manually operated connector devices such as connectors 31 and 37 at the ends of effluent fluid tubing 70 for being connected to a hemofilter and waste bag 34, connectors 21 and 23 for connecting the ends of saline fluid tubing 83 to a saline bag (not shown), and blood tubing 22 and connectors 26 and 28 for connecting the blood fluid tubing 22 and 72 to hemofilter 25 (FIG. 1). Needle and catheter assembly components 36 and 75 at the ends of the blood tubing 22 for patient blood access and patient blood return tubing 72 are shown. Connector 33 connects dialysate fluid tubing 90 to the hemofilter and connector 39 to a dialysate bag (not shown). Examples of such connectors include clips, clamps, threaded and quick-disconnect connectors and other releasable fittings allowing a therapist or physician to easily, manually, efficiently and selectively change filters as well as tubing panels, as required or desired.

Figure 6A:
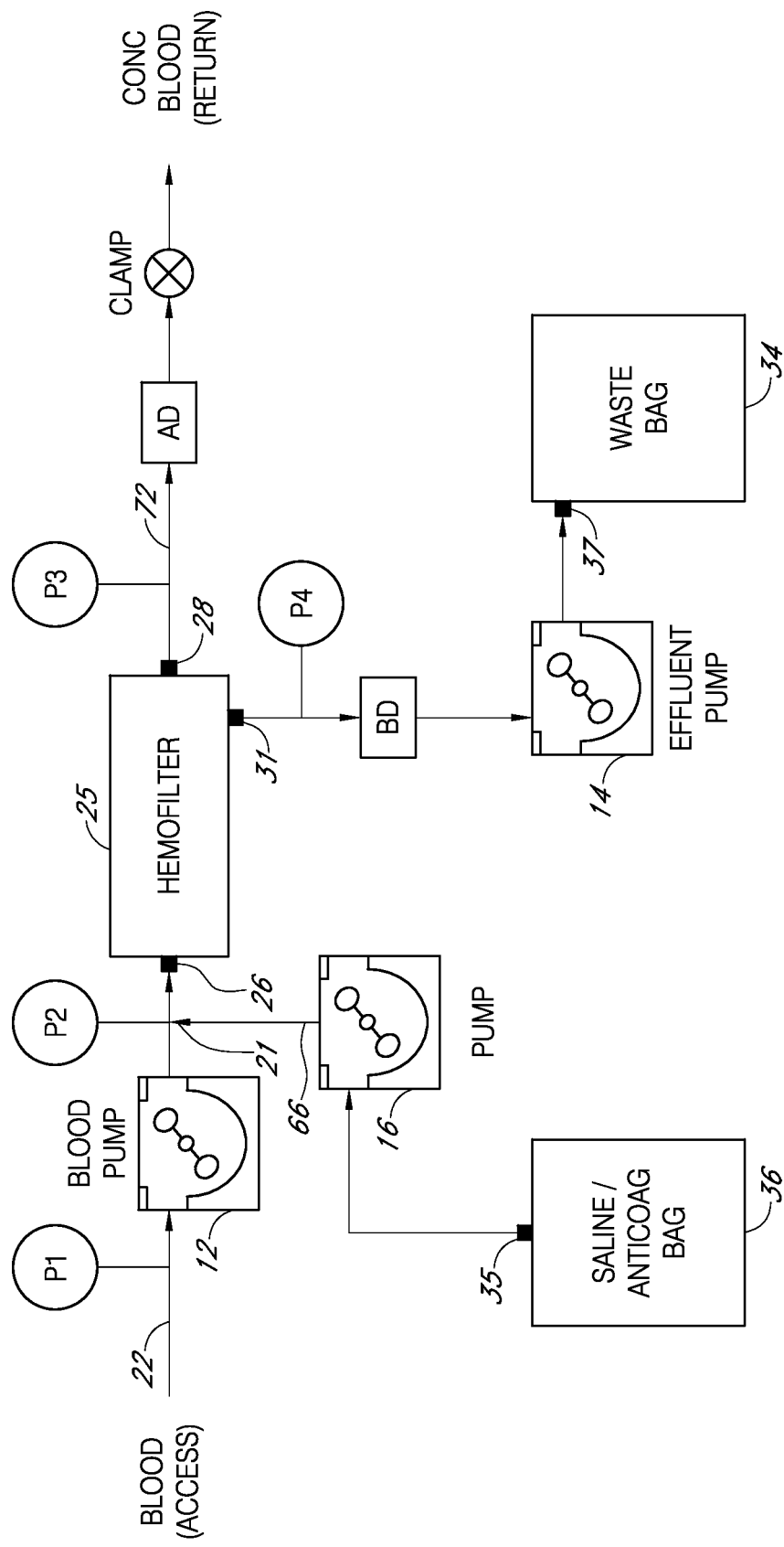
FIGS. 6A, 6B, 7 and 8 schematically show components of the apparatus configured for carrying out selected blood filtration therapies.

FIGS. 6A, 7 and 8 schematically illustrate different blood therapies and treatments which may be carried out using different panel and tubing sets and different hemofilter columns as described above. For removing plasma water in a single stage, the hemofilter selected may be an ultrafilter cartridge, the blood panel and tubing connected between a patient blood access and return and to the ultrafilter. The fluid tubing panel is configured to engage effluent pump 14 to direct plasma water from the ultrafilter to the waste bag, and to pump 16 for directing saline from a bag 36 to blood tubing 22 upstream from the ultrafilter to dilute the blood prior to ultrafiltration. Alternatively, the saline fluid tubing may be connected to the ultrafilter. It may be desirable also to add an anticoagulant such as heparin, a citrate, or other known anticoagulant to the saline fluid. Blood pump 12 pumps blood through the blood tubing 22 from the patient to the ultrafilter and then to a patient return device.

FIG. 7 illustrates operation of an apparatus embodiment in which the hemofilter is configured to remove metabolic waste via diffusion as well as excess fluid or plasma water via convection. The system pumps blood through the hemofilter cartridge and dialysate at counter flow to the blood outside of the filtration membrane. The system pumps the dialysate and excess fluid into a waste bag and concentrated blood is returned to the patient. Thus, in addition to the components illustrated in FIG. 6A, the fluid tubing panel includes tubing configured to engage dialysate pump 18 which directs the dialysate from bag 38 to the hemofilter. Such combination of hemofilter and fluid and blood panels allows the apparatus to operate to perform hemodialysis or hemodiafiltration.

The apparatus configuration shown in FIGS. 6A and 7 and described above may be modified to direct saline or replacement fluid into the patient blood return line downstream from the hemofilter. Thus, instead of pumping fluid from bag 36 to blood supply tubing 22 upstream from filter 25, the saline supply tubing may be configured to direct the saline, replacement fluid, plasma and/or albumin to the filtered blood being returned to the patient. Typical commercially available replacement fluids contain electrolytes such as chloride salts of calcium, magnesium, potassium and sodium, sodium bicarbonate, proteins and other nutrients such as lactic acid and dextrose. The selection of suitable replacement fluids and their use are well known to those skilled in the art. Such an embodiment may be provided by installing an additional length of tubing (not shown) between fluid tubing section 66 and blood tubing 72. Pinch clamps (not shown) may be installed along the added tubing and tubing section 66 to allow an operator to close either of the saline supply tubes thereby selectively directing the saline or replacement fluid upstream and/or downstream from the hemofilter. Other alternative components such as a valve at the junction of the added tubing with tubing section 66 may be used.

An alternative system embodiment using five pumps is illustrated in FIG. 8. Anticoagulant is introduced upstream from the hemofilter and replacement fluid is added downstream from the hemofilter. In the system shown, a small amount or bolus of anticoagulant may be periodically supplied to the blood stream in amounts sufficient for regional effect to prevent or reduce clotting along the blood inlet tubing and at the filter membrane. Anticoagulant pump 16 cooperates with fluid supply tubing 66 which may be connected to blood supply tubing 22 or directly attached to the hemofilter. Replacement fluid is pumped from replacement fluid bag 74 to blood supply tubing 72 by pump 76.

Figure 6B:
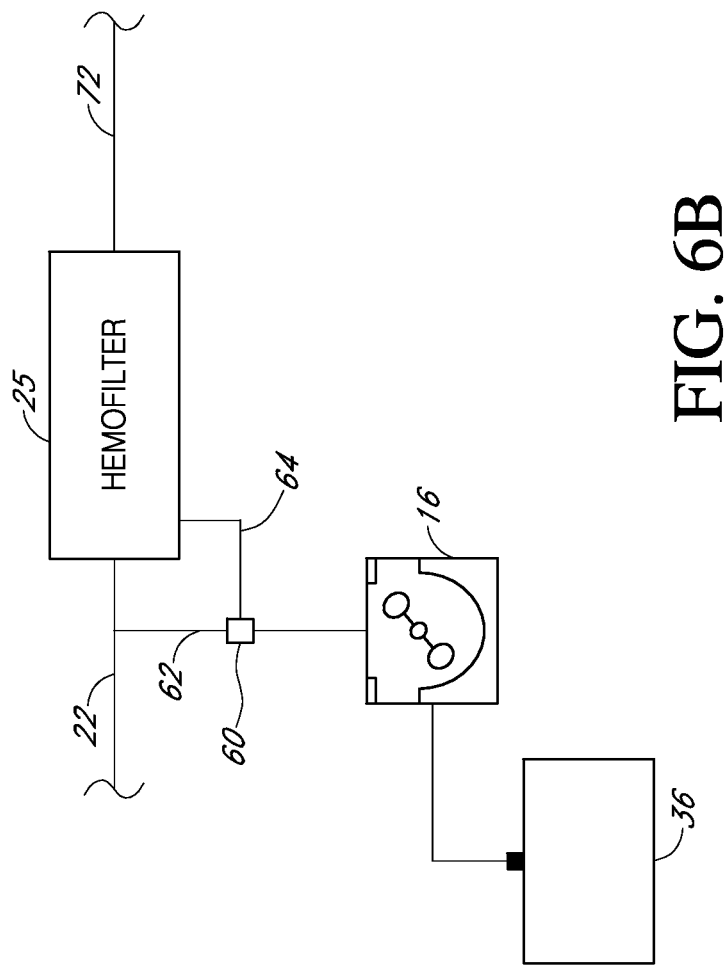

The apparatus may also be configured to accomplish a backflush of an ultrafilter membrane. The backflush may be accomplished on a selected or periodic backflush cycle, or it may be accomplished in response to detection of transmembrane pressure of the filter cartridge or other sensing of clogging of the membrane pores. For example, the system may include one or more pressure transducers for monitoring pressure of the plasma waste fluid as an indication of when the filter pores are becoming clogged to an extent necessary to terminate the wastewater extraction and initiate backflushing. FIG. 6B illustrates schematically a portion of the apparatus of FIG. 6A which is modified by incorporating a selectively operated valve 60 in the fluid line which directs saline from the saline bag 36 to the hemofilter or ultrafilter 25. Such an apparatus embodiment may be operated to initiate backflush by temporarily terminating the pumping of blood to the filter cartridge 25 via blood tubing 22 and operating valve 60 so as to temporarily stop the flow of the saline to blood tubing 22 via fluid tubing section 62 and instead directing the saline fluid into the filter cartridge on the outside of the filter membrane. The bolus of a backflush fluid will be of a volume and duration sufficient to perform the desired backflush, after which valve 60 is again operated to direct the flow of the saline to blood tubing 22 and the blood pump again operated to begin blood therapy procedures. Other details for such a backflushing may be understood by referring to U.S. Pat. No. 6,659,973, the description of which is incorporated herein by reference in its entirety. Again, the backflush procedure and embodiment is optional.

The multiple panel assembly may also be used for carrying out plasma separation, plasmapheresis, plasma exchange, liver support and therapeutic apheresis. Such plasma separation and treatment configuration will utilize similar configurations as described and shown in the figures previously discussed. However, the hemofilter or ultrafilter will be replaced by a plasma separation cartridge in which plasma is separated from whole blood from the patient. The recovered plasma is thereafter discarded and replaced, or the plasma is treated for separation and removal and/or neutralization of selected disease-related components or other substances such as poisons, toxins or drugs, etc. In FIG. 9, the system illustrated is configured to carryout plasma replacement. Plasma from a patient is pumped to a plasma separation cartridge 85 where plasma is separated across the cartridge membrane or membranes and pumped by a plasma pump 87 to plasma waste bag 88. Replacement plasma from plasma infusion bag 84 is pumped with a third fluid pump, second plasma pump 86, to the patient blood return tubing 72. An anticoagulant source and pump are also shown and which components are operated and function as previously described. One fluid pump will pump anticoagulant to the blood supply tubing 22 upstream from a plasma separation cartridge and a second fluid pump will direct separated plasma to a plasma waste bag.

Figure 10:
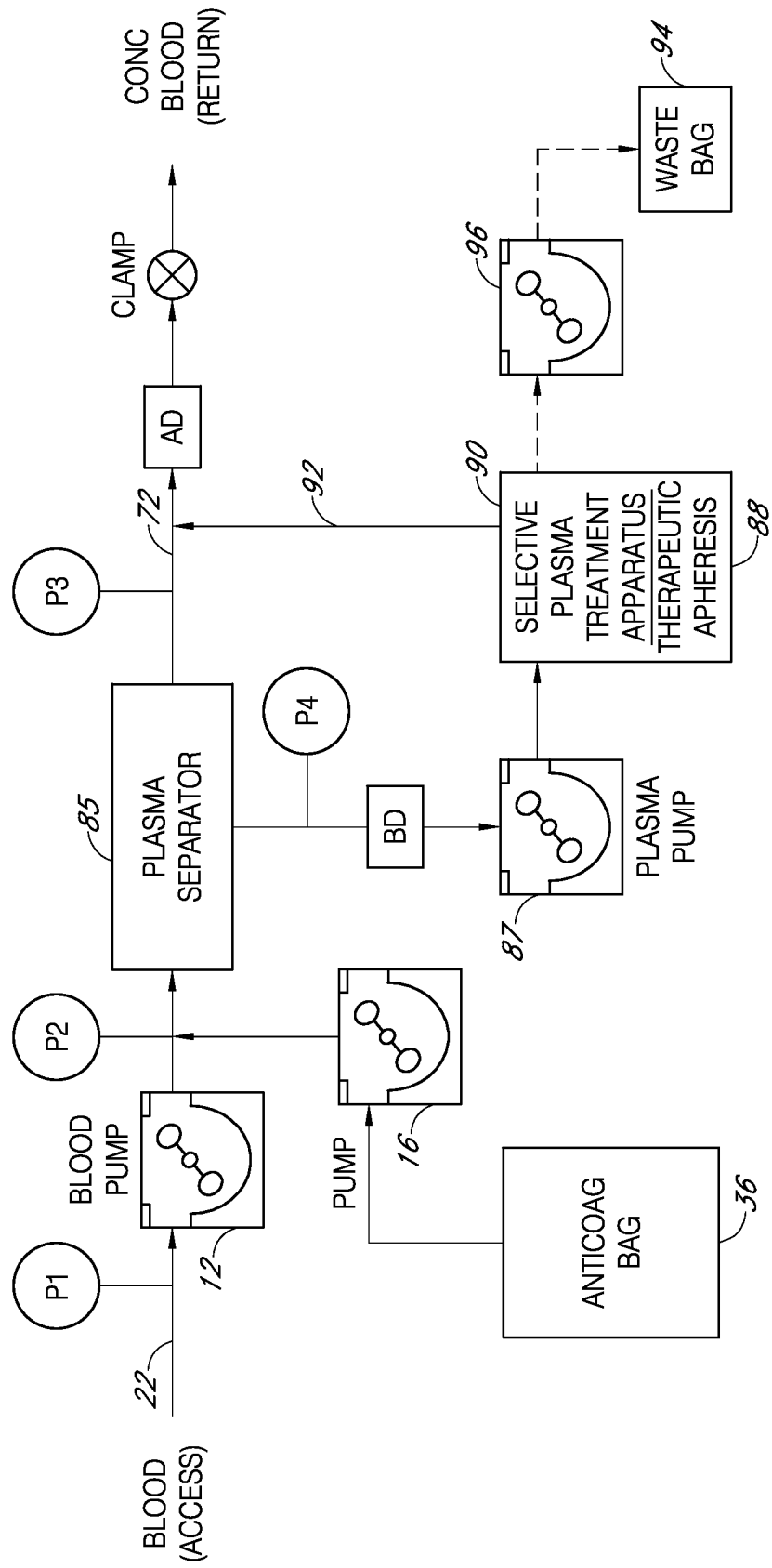

FIG. 10 illustrates an embodiment of the apparatus for processing separated plasma for selective plasma treatment. Such selective plasma treatment is referred to as therapeutic apheresis, and includes apparatus capable of selectively removing disease-related components such as toxins, antibodies, proteins, pathogens including bacteria, virus, etc. as well as removing or neutralizing drugs, poisons, or other selected chemical substances. As shown in FIG. 10, a selective plasma treatment apparatus or therapeutic apheresis apparatus 90 is supplied with separated plasma via plasma pump 87 for treating the plasma. Such selective treatment apparatus may include plasma exchange components, centrifugal or membrane-separation filters, cascade or multiple filtration membranes and columns, one or more absorption cartridges capable of absorbing specific disease-related components or drugs, and activated charcoal cartridges. Other examples of such selective component removal apparatus includes specialized columns incorporating compositions such as cross-linked polyvinyl alcohol gel beads or microporous cellulose beads for removing specific amino acid ligands and antibodies. Other examples are components capable of chemically processing the plasma to precipitate heparin, salt-amino acids, or for effectively neutralizing drugs, poisons or disease-related components in the plasma. Such apparatus may be used for liver support functions as well. Moreover, the selective plasma treatment apparatus may combine different plasma treatment components used in series or parallel for simultaneously or concurrently carrying out multiple plasma treatment or therapy where such need is indicated. The treated plasma is directed to the patient via tubing 92 connected to patient blood return line 72. If needed, a separate fourth fluid pump may be used for pumping the treated plasma to the patient return line or to an effluent container. In FIG. 10, a supplemental fluid pump 96 is also shown for directing waste fluid from the selective plasma treatment apparatus 90 to a waste bag 94. Such an optional effluent or waste fluid component may be used where the selective plasma treatment apparatus 90 separates plasma components from the plasma which are to be discarded. Additional description of selective component removal apparatus and technologies are described in U.S. Pat. No. 6,849,183, the relevant portions thereof which are incorporated herein by reference, as well as in *Therapeutic Apheresis*, Vol. 1, No. 2, May 1997, pages 135-146. Other examples of such cartridges or plasma exchange components, filters, etc. are disclosed in U.S. Pat. No. 5,605,627, the relevant portions of which are incorporated herein by reference. The selective plasma treatment apparatus may be designed to allow an operator to exchange, replace or modify the configuration of the filters, columns, cartridges, etc. in order to accomplish different plasma treatments on a patient, if desired.

The systems described hereinabove allows the physician or therapist the flexibility of selecting and mixing and matching different hemofilter, plasma replacement or plasma treatment columns with different fluid tubing set configurations for any selected CRRT therapy and/or plasma separation and plasma treatment using the same blood tubing set. Thus, the apparatus can be modified to perform different, alternate therapies on a single patient without disturbing the blood tubing connections as well as to efficiently and economically reconfigure the system for different patients.

What is claimed is:

1. Apparatus for performing blood therapy comprising:
 a housing having a first side, a second side and a front cover separating said first and second sides and extending therebetween, said first side having a blood pump secured thereon for engaging a blood tube and said second side having a plurality of fluid pumps secured thereon for engaging fluid tubing;
 a first panel removably mounted on the exterior of said first side of said housing and having first tubing secured thereon configured to engage and cooperate with said blood pump for directing blood pumped therethrough;
 a second panel independent of said first panel removably mounted on the exterior of said second side of said housing and having second tubing secured thereon configured to engage and cooperate with said plurality of fluid pumps for directing fluid pumped therethrough;
 a filter cartridge removably mounted on said housing;
 computer sensible identification on each of said first panel, said second panels, and said filter cartridge; and
 a controller within the housing configured to read said computer sensible identification, the controller identifying said first panel, said second panel, and said filter cartridge based on the computer sensible identification thereon and operating said blood pump and said fluid pumps in response to said computer sensible identification.

2. Apparatus of claim 1, further comprising a third panel independent of said first and said second panels and mounted on the front cover of said housing.

3. Apparatus of claim 2 further comprising a computer sensible filter cartridge identification on said third panel.

4. Apparatus of claim 1 wherein the controller further comprises a screen cooperating with said controller and configured to display the identification of the first and second panels and the filter cartridge.

5. Apparatus of claim 4 wherein one of said fluid pumps comprises an effluent pump, and a waste container for receiving fluid removed from blood during blood therapy and wherein said second tubing is configured to engage said effluent fluid pump when said second panel is installed and cooperate therewith to direct fluid removed from blood to said waste container.

6. Apparatus of claim 5 wherein said filter cartridge comprises an ultrafilter releasably connected to and in fluid communication with said first tubing and said second tubing.

7. Apparatus of claim 6 wherein said second tubing is configured to engage and cooperate with an effluent fluid pump to pump plasma water from said ultrafilter to said waste container.

8. Apparatus of claim 7 wherein one of said fluid pumps comprises a saline fluid pump, and a fluid supply container containing saline, anticoagulant or replacement fluid or mixtures of two or more thereof and whereby said second tubing is in fluid communication with said fluid supply container and is configured to engage said saline fluid pump and to cooperate therewith for pumping saline or replacement fluid from said supply container to said first tubing upstream from said ultrafilter or to said ultrafilter.

9. Apparatus of claim 1 wherein said first tubing is configured for directing blood to and from said filter cartridge and said second tubing is configured for directing fluid to said first tubing and/or said filter cartridge and for directing fluid from said filter cartridge.

10. Apparatus of claim 5 wherein said filter cartridge comprises a hemofilter releasably connected to and in fluid communication with said first tubing and said second tubing.

11. Apparatus of claim 10 wherein one of said fluid pumps comprises a dialysate fluid pump, and a dialysate fluid container having dialysate fluid therein and wherein said second tubing is in fluid communication with said dialysate fluid container and is configured to engage and cooperate with said dialysate fluid pump to pump dialysate fluid from said dialysate fluid supply container to said hemofilter.

12. Apparatus of claim 11 wherein said second tubing and said effluent fluid pump engage and cooperate to pump dialysate fluid and fluid removed from blood from said hemofilter to said waste container.

13. Apparatus of claim 12 wherein said hemofilter is configured to remove plasma water from blood by convection and to remove toxic waste from blood by diffusion.

14. Apparatus of claim 12 wherein one of said fluid pumps comprises a saline fluid pump, and a fluid supply container containing saline, anticoagulant or replacement fluid or mixtures of two or more thereof and whereby said second tubing is in fluid communication with said fluid supply container and is configured to engage said saline fluid pump and cooperate therewith for pumping saline or replacement fluid from said supply container to said first tubing upstream from said hemofilter or to said hemofilter.

15. Apparatus of claim 7 wherein said second tubing is in selective communication with said first tubing upstream and/or downstream from said ultrafilter whereby said saline or replacement fluid is selectively directed via said second tubing to said first tubing upstream and/or downstream from said ultrafilter.

16. Apparatus of claim 13 wherein said second tubing is in selective communication with said first tubing upstream and/or downstream from said ultrafilter whereby said saline or replacement fluid is selectively directed via said second tubing to said first tubing upstream and/or downstream from said hemofilter.

17. Apparatus of claim 11 wherein one of said fluid pumps comprises a replacement fluid pump, and a replacement fluid container having replacement fluid therein and wherein said second tubing is in fluid communication with said replacement fluid container and is configured to engage and cooperate with said replacement fluid pump to pump replacement fluid from said container to said first tubing downstream from said hemofilter.

18. Apparatus of claim 17 wherein one of said fluid pumps comprises an anticoagulant fluid pump, and a container of anticoagulant fluid and whereby said second tubing is in fluid communication with said anticoagulant fluid container and is configured to engage and cooperate with said anticoagulant fluid pump to pump anticoagulant fluid to said hemofilter or to said first tubing upstream from said hemofilter.

19. Apparatus of claim 17 wherein one of said fluid pumps comprises a saline fluid pump, and a fluid supply container containing saline or anticoagulant fluid or two or more thereof and wherein said second tubing is in fluid communication with said fluid supply container and is configured to engage a saline fluid pump, and wherein said second tubing is in selective communication with said first tubing and said hemofilter whereby said second tubing cooperates with said saline pump for selectively directing saline or anticoagulant fluid to said first tubing or to said hemofilter.

20. Apparatus of claim 18 wherein one of said fluid pumps comprises a saline fluid pump, and a fluid supply container containing saline or anticoagulant fluid or two or more thereof and wherein said second tubing is in fluid communication with said fluid supply container and is configured to engage a saline fluid pump, and wherein said second tubing is in selective communication with said first tubing and said hemofilter whereby said second tubing cooperates with said saline pump for selectively directing saline or anticoagulant fluid to said first tubing or to said hemofilter.

21. Apparatus of claim 5 wherein said filter cartridge comprises a plasma separation cartridge and said apparatus includes a replacement plasma container and a plasma pump for pumping replacement plasma therefrom, and wherein said second tubing is configured to direct replacement plasma from said replacement plasma container to said first tubing downstream from said plasma separation cartridge.

22. Apparatus of claim 21 wherein one of said fluid pumps comprises an anticoagulant fluid pump, and a container of anticoagulant fluid and whereby said second tubing is in fluid communication with said anticoagulant fluid container and is configured to engage and cooperate with said anticoagulant fluid pump to pump anticoagulant fluid to said plasma separation cartridge or to said first tubing upstream from said plasma separation cartridge.

23. Apparatus of claim 1 wherein said filter cartridge comprises a plasma separation cartridge and said apparatus further comprises therapeutic apheresis apparatus configured for removing and/or separating selected disease-related components from separated plasma, and wherein one of said fluid pumps comprises a plasma pump for pumping separated plasma from said plasma separation cartridge to said therapeutic apheresis apparatus.

24. Apparatus of claim 23 wherein one of said fluid pumps comprises an anticoagulant fluid pump, and a container of anticoagulant fluid and whereby said second tubing is in fluid communication with said anticoagulant fluid container and is configured to engage and cooperate with said anticoagulant fluid pump to pump anticoagulant fluid to said plasma separation cartridge or to said first tubing upstream from said plasma separation cartridge.

25. Apparatus of claim 23 or 24 wherein said therapeutic apheresis apparatus comprises a plasma exchange assembly.

26. Apparatus of claim 23 or 24 wherein said therapeutic apheresis apparatus comprises a multiple stage filtration assembly.

27. Apparatus of claim 23 or 24 wherein said therapeutic apheresis apparatus comprises one or more columns or cartridges containing materials for selectively absorbing disease-related components, drugs, poisons or chemicals passing therethrough.

28. Apparatus of claim 23 or 24 wherein said therapeutic apheresis apparatus comprises one or more reactors containing compositions for reacting with and/or neutralizing selective disease-related components, drugs, poisons or chemicals in the separated plasma.

29. Apparatus of claim 8 including a switchable valve cooperating with said second tubing for selectively directing saline fluid to said first tubing or said ultrafilter and wherein said controller is programmed to selectively operate said valve.

30. Apparatus of claim 8 wherein said controller is programmed to periodically interrupt operation of said blood pump and concurrently switch said valve to direct saline fluid to back flush said ultrafilter.

31. Apparatus of claim 1 wherein said first panel and said second panel are configured for being mounted independently on said housing.

32. Apparatus of claim 2 wherein said filter cartridge is secured on said third panel.

33. Apparatus of claim 32 wherein said first panel and said second panel are connected to said third panel.

34. Apparatus of claim 33 further comprising hinges or flexible connectors connecting said third panel to said first panel and said second panel.

35. Apparatus of claim 1 wherein said housing comprises panel support members extending therefrom configured for mounting and supporting said panels.

36. Apparatus of claim 34 wherein said housing comprises panel support members extending therefrom configured for mounting and supporting said panels.

37. Apparatus of claim 1 wherein each of said first panel and said second panel comprise a transparent or translucent plastic configured to allow observation of said tubing therethrough.

38. Apparatus of claim 1 wherein each of said first panel and said second panel include one or more ports thereon configured for access to and/or observation of apparatus components and/or said tubing.

39. A panel assembly configured to be manually mounted on the exterior of a blood therapy apparatus housing comprising a first side having a blood pump secured thereon, a second side having a plurality of fluid pumps secured thereon and a front cover separating said first and said second sides and extending therebetween, said panel assembly comprising:
   a first panel having first tubing secured thereon configured to engage and cooperate with said blood pump for directing blood pumped therethrough;
   a second panel independent of said first panel having second tubing secured thereon configured to engage and cooperate with said plurality of fluid pumps for directing fluid pumped therethrough;
   a third panel independent of said first and said second panels; and
   hinges or flexible connectors connecting said third panel to said first panel and said second panel; and
   computer sensible identification on each of said first panel, said second panel, and said third panel for identifying said first panel, said second panel, and said third panel to a controller for operating said blood pump and said fluid pumps in response to said computer sensible identification.

40. The panel assembly of claim 39 wherein said third panel includes components for securing a blood filter cartridge or plasma separation cartridge thereon.

41. The panel assembly of claim 39 wherein each of said first panel and said second panel comprise a transparent or translucent plastic configured to allow observation of said tubing therethrough.

42. The panel assembly of claim 39 wherein each of said first and said second panels include one or more ports formed thereon for access to and/or observation of blood therapy apparatus components and blood or fluid tubing.

43. A panel assembly of claim 39 wherein
   said first panel comprises a generally flat, planar panel having blood supply tubing mounted thereon, said blood supply tubing comprising first blood tubing configured to engage a peristaltic blood pump and having connectors configured to releasably connect a first end thereof to a device for directing blood from a patient and to releasably connect a second end thereof to an inlet of a blood filtering cartridge or plasma separation cartridge and second blood tubing and having connectors configured to releasably connect a first end thereof to an outlet of a blood filtering cartridge or plasma separation cartridge and releasably connect a second end thereof to a device for returning blood to a patient; and
   said second panel comprises a generally flat, planar panel having fluid supply tubing mounted thereon comprising first fluid tubing configured to engage a peristaltic fluid pump and having connectors configured to releasably connect a first end thereof to an outlet of a blood filter cartridge or a plasma separation cartridge to releasably connect a second end thereof to a fluid collection container or to therapeutic apheresis apparatus, and second fluid tubing configured to engage a peristaltic fluid pump and having connectors configured to releasably connect a first end thereof to said first blood tubing or to an inlet of a blood filter cartridge and to connect a second end thereof to a fluid supply container, and
   wherein said third panel has a blood filter cartridge or a plasma separation cartridge mounted thereon.

44. A panel assembly of claim 43 wherein said fluid supply tubing further comprises third fluid tubing configured to engage a peristaltic fluid pump and having connectors configured to releasably connect a first end thereof to a dialysate fluid supply container and releasably connect a second end thereof to a blood filter cartridge.

45. A panel assembly of claim 44 wherein said fluid supply tubing further comprises fourth fluid tubing configured to engage a peristaltic fluid pump and having connectors configured to releasably connect a first end thereof to a replacement fluid supply container or plasma supply container and releasably connect a second end thereof to said second blood supply tubing.

46. A panel assembly of claim 43 wherein said fluid supply tubing further comprises third fluid tubing configured to engage a peristaltic pump and having connectors configured to releasably connect a first end thereof to therapeutic apheresis apparatus and releasably connect a second end thereof to said second blood supply tubing.

47. Apparatus of claim 1, wherein the second panel enables modification of the second tubing secured thereon without disturbing said blood tubing connection to a patient.

48. Apparatus of claim 39, wherein the second panel enables modification of the second tubing secured thereon without disturbing said first tubing connection to a patient.

49. Apparatus of claim 1, further comprising a sensor configured to identify the first panel, the second panel, and the filter cartridge based on the computer sensible identification thereon.

* * * * *